(12) United States Patent
Papangelou et al.

(10) Patent No.: US 11,160,546 B2
(45) Date of Patent: Nov. 2, 2021

(54) EXPANDING IMPLANT AND METHOD OF TISSUE FIXATION

(71) Applicant: Arthrex, Inc., Naples, FL (US)

(72) Inventors: Christopher G. Papangelou, Bonita Springs, FL (US); Kenneth T. Helenbolt, Naples, FL (US); Jacob A. Jolly, Naples, FL (US); Justin Boyle, Naples, FL (US)

(73) Assignee: Arthrex, Inc., Naples, FL (US)

( * ) Notice: Subject to any disclaimer, the term of this patent is extended or adjusted under 35 U.S.C. 154(b) by 385 days.

(21) Appl. No.: 16/508,879

(22) Filed: Jul. 11, 2019

(65) Prior Publication Data

US 2021/0007729 A1 Jan. 14, 2021

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/044* (2013.01); *A61B 2017/0451* (2013.01); *A61B 2017/0453* (2013.01); *A61F 2002/0823* (2013.01)

(58) Field of Classification Search
CPC .............. A61B 17/04; A61B 17/0401; A61B 2017/044; A61B 2017/0451; A61B 2017/0453; A61F 2/08; A61F 2/0811; A61F 2002/0823; A61F 2002/0835; A61F 2002/0858

See application file for complete search history.

(56) References Cited

U.S. PATENT DOCUMENTS

| | | | |
|---|---|---|---|
| 6,554,862 | B2 | 4/2003 | Hays et al. |
| 7,329,281 | B2 | 2/2008 | Hays et al. |
| 8,048,158 | B2 | 11/2011 | Hays et al. |
| 8,317,863 | B2 | 11/2012 | Cauldwell et al. |
| 8,747,469 | B2 | 6/2014 | Wang et al. |
| 8,870,877 | B2 | 10/2014 | Koogle, Jr. |
| 9,044,313 | B2 | 6/2015 | Heaven |
| D740,427 | S | 10/2015 | McDonnell et al. |
| 9,265,600 | B2 | 2/2016 | Niese et al. |
| 9,775,597 | B2 | 10/2017 | Heaven et al. |
| 2004/0230194 | A1 | 11/2004 | Urbanski et al. |
| 2018/0161146 | A1 | 6/2018 | Beck, Jr. et al. |
| 2019/0117377 | A1* | 4/2019 | Ticker ............ A61F 2/0811 |

FOREIGN PATENT DOCUMENTS

EP 1 297 799 A2 4/2003
FR 2622430 A1 5/1989

* cited by examiner

*Primary Examiner* — George J Ulsh
(74) *Attorney, Agent, or Firm* — Blank Rome LLP

(57) ABSTRACT

This disclosure relates to expandable implants and methods of using expandable implants for tissue fixation and repair.

20 Claims, 5 Drawing Sheets

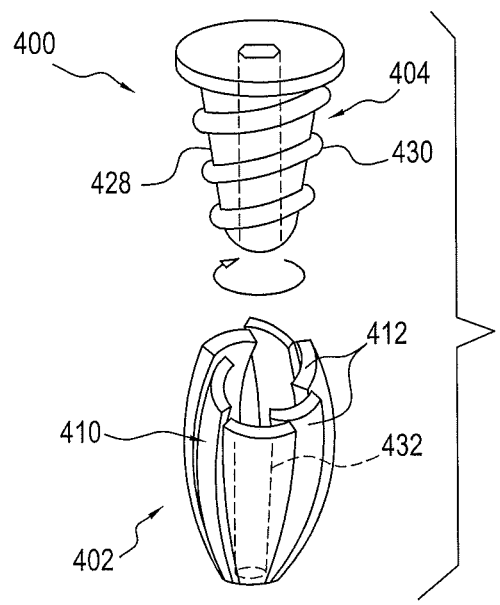
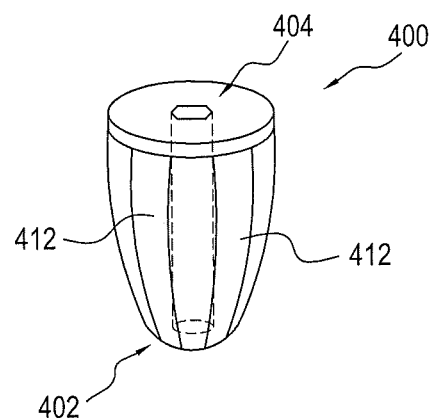
FIG. 4A  FIG. 4B
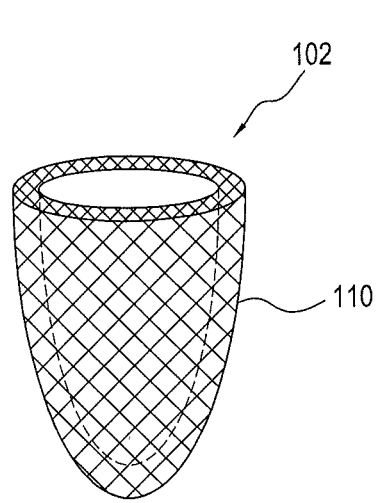
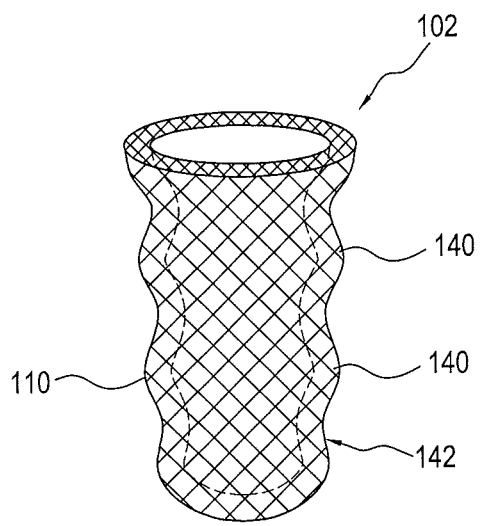
FIG. 5  FIG. 6

EXPANDING IMPLANT AND METHOD OF TISSUE FIXATION

BACKGROUND

When soft tissue tears away from bone, reattachment becomes necessary. This disclosure relates to expandable implants and methods of using expandable implants for tissue fixation and repair.

SUMMARY

This disclosure relates to a tissue fixation implant that comprises, inter alia, a compressible sheath that has a body configured to capture tissue, and the body has opposite proximal and distal ends. The body is compressible along a longitudinal axis of the sheath from a first position, in which the body is not compressed, to a second position, in which the body is compressed and radially expanded. An expansion member may be receivable in the body of the sheath and has an insertion end and a head end opposite the insertion end. At least the insertion end of the body has an engagement feature configured to engage the distal end of the body of the sheath and move the distal end of the body along the longitudinal axis of the sheath from the first position, in which the body is not compressed, to a second position, in which the body is compressed and radially expanded.

BRIEF DESCRIPTION OF THE DRAWINGS

FIGS. 4A and 4B are exploded and assembled elevational view, respectively, of an example expanding implant using a central screw to expand the outer sheath;

FIG. 5 is of an elevational view of an example sheath constructed from a textile alone or combination textile/polymer as an example expanding implant;

FIG. 6 is of an elevational view of an example sheath of an example expanding implant.

DETAILED DESCRIPTION

Figure 1A:
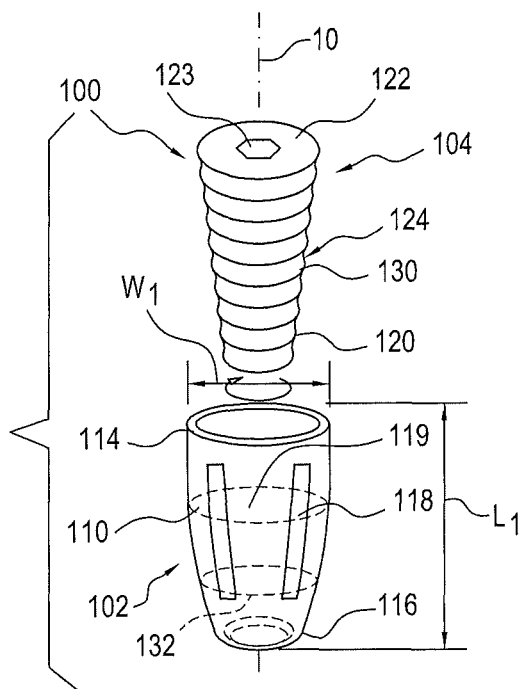
FIG. 1A is an exploded elevational view of an example expanding implant.

This disclosure relates to a tissue fixation implant that comprises, inter alia, a compressible sheath that has a body configured to capture tissue, and the body has opposite proximal and distal ends. The body is compressible along a longitudinal axis of the sheath from a first position, in which the body is not compressed, to a second position, in which the body is compressed and radially expanded. In an embodiment, the body of the sheath includes one or more longitudinal slots radially spaced from one another, the one or more longitudinal slots being closed at the proximal and distal ends of the body and configured to allow radial expansion of the body. In an embodiment, the sheath is formed of a polymer. Alternatively, the sheath may be formed of a textile or a textile embedded with a polymer.

An expansion member may be receivable in the body of the sheath and has an insertion end and a head end opposite the insertion end. In an embodiment, the maximum outer diameter of the expansion member is equal to or less than the minimum inner diameter of the body of the sheath.

At least the insertion end of the body has an engagement feature configured to engage the distal end of the body of the sheath and move the distal end of the body along the longitudinal axis of the sheath from the first position, in which the body is not compressed, to a second position, in which the body is compressed and radially expanded.

In an embodiment, the outer threads of the expansion member are configured to engage inner threads on an inner diameter of the body of the sheath.

In an embodiment, a thread pitch of the distal threads is different than a thread pitch of the proximal threads such that engagement of the distal and proximal threads moves the distal end of the body of the sheath to the second position.

In an embodiment, the head end of the expansion member has a shoulder for abutting the proximal end of the body of the sheath.

In an embodiment, the body of the sheath is embedded with absorbable or non-absorbable polymer.

In an embodiment, the body of the sheath is formed of a mesh overmolded with an absorbable or non-absorbable polymer.

In an embodiment, the body of the sheath is formed of one or more sutures.

In an embodiment, the sheath has various thicknesses.

In an embodiment, the compressible sheath is configured for installation in a bone tunnel in an insertion direction and the engagement feature of the expansion member moves the distal end of the body of the sheath in a direction opposite the insertion direction when moving the body of the sheath from the first position to the second position.

In an embodiment, the body may have opposite proximal and distal ends and a plurality of collapsible forms allowing the sheath to collapse from a first position, in which the body is not compressed, to a second position, in which the body is compressed. An expansion member may be receivable in the body of the sheath. The expansion member has an insertion end and a head end opposite the insertion end. The expansion member has an outer surface that tapers inwardly from the head end to the insertion end, and the outer surface of the expansion member may have an engagement feature configured to engage an inside of the body of the sheath. Insertion of the expansion member into the body of the sheath radially expands the plurality of collapsible forms.

In an embodiment, the plurality of collapsible forms is wave forms that collapse longitudinally to move the sheath along a longitudinal axis thereof to the second position.

In an embodiment, the plurality of collapsible forms is radially collapsible forms that collapse inwardly to compress the sheath.

This disclosure also relates to a method of tissue fixation, comprising the steps of, inter alia, installing a compressible sheath of an implant into a bone tunnel to capture tissue between the sheath and the bone tunnel; and then inserting an expansion member in a body of the sheath in an insertion direction, such that the expansion member engages a distal end of the sheath and compresses the body along a longitudinal axis of the sheath in a direction opposite the insertion direction, thereby radially expanding the body of the sheath for fixation of the tissue in the bone tunnel.

In an embodiment, the step of inserting the expansion member into the body of the sheath includes threadably engaging an insertion end of the expansion member with the distal end of the sheath.

In an embodiment, outer threads of the expansion member that engage inner threads of the body of the sheath have a different thread pitch than that of the inner threads such that the expansion member pulls the distal end in the direction opposite the insertion direction.

Conventional fixation devices have limitations, including tunnel widening, joint laxity, slippage of the device within the femoral tunnel, slippage of the graft ligament relative to the device, or damage to the graft ligament resulting from contact with the device itself, such as the graft ligament being lacerated or wound up causing the graft orientation to be altered by the device. Thus, disclosed embodiments provide a solution for tissue ligament fixation devices to securely attach tissue to bone without damage to the tissue.

Referring to the figures, this disclosure generally relates to expanding implants and associated methods of use for tissue fixation. The term "tissue" may include any soft tissue, ligaments, tendons, and the like, or grafts for the same. The expanding implants of this disclosure have a simple design that is easy to use for tissue fixation, while also securely fixing the tissue to bone.

Figure 1B:
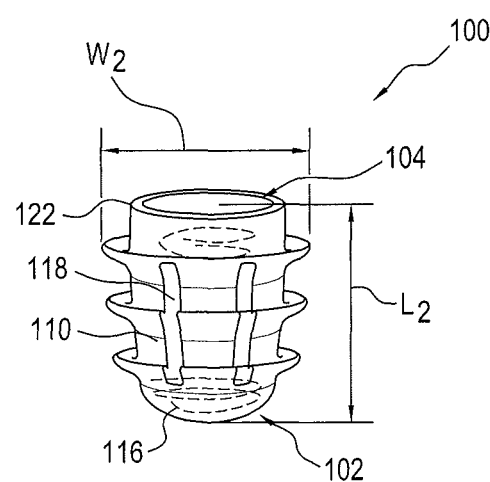
FIG. 1B is an elevational assembled view of the expanding implant illustrated in FIG. 1A.
Figure 1C:
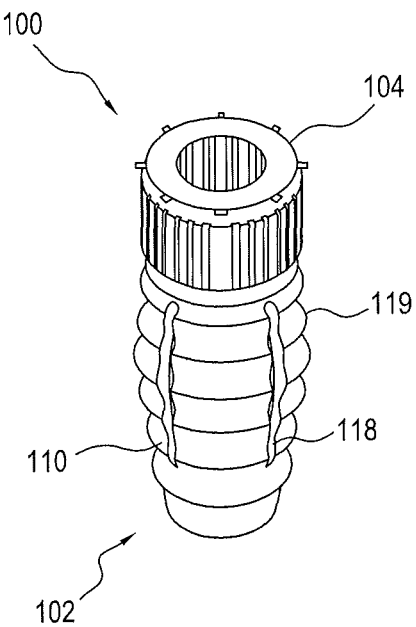
FIG. 1C is a perspective view of the expanding implant illustrated in FIG. 1A, showing the sheath compressed longitudinally and expanded radially.

As seen in FIGS. 1A-1C, an expanding implant 100 of an embodiment of this disclosure generally comprises a compressible sheath 102 and an expansion member 104 receivable in the sheath 102 for compressing and radially expanding the sheath 102 to fix tissue to bone. The sheath 102 has a body 110 that is configured to capture tissue between its outer surface 112 (FIG. 9) and the bone. The body 110 has opposite proximal and distal ends 114 and 116, respectively. The body 110 is compressible along the longitudinal axis 10 of the sheath 102 from a first position, in which the body is not compressed (FIG. 1A), such as when the sheath 102 is installed into a bone tunnel 90 (FIG. 7), to a second position, in which the body 110 has buckled, and is compressed and radially expanded (FIGS. 1B and 1C), such as for fixing the tissue to the bone tunnel 90. The length $L_1$ of the body 110 when the sheath 102 is in the first position is greater than the compression length $L_2$ of the body 110 when the sheath 102 is in the second position. And the width $W_1$ of the body 110 when in the first position is less than the width $W_2$ of the body 110 when in the second position.

The body 110 of the sheath 102 has one or more longitudinal slots 118 configured to allow radial expansion of the body 110 when compressed. In an embodiment, the one or more longitudinal slots 118 are closed at the proximal and distal ends 114 and 116, respectively, of the body 110. As seen in FIG. 1C, when the sheath 102 is compressed by advancement of the expansion member 104, the sections 119 of the body 110 of the sheath created by the longitudinal slots 118 can expand radially outwardly.

Expansion member 104 comprises an insertion end 120, a head end 122 opposite the insertion end, and an engagement feature 124 for engaging the sheath 102. In an embodiment, the engagement feature 124 is located at least on the insertion end 120. Engagement feature 124 is configured to engage the distal end 116 of the body 110 of the sheath 102 to move the body's distal end 116 along the longitudinal axis 10 of the sheath from its first non-compressed position toward the opposite proximal end 114 of the body 110 to the second compressed position. The sheath 102 may be installed in the bone tunnel 90, for example, in an insertion direction and the engagement feature 124 moves the distal end 116 of the body of the sheath 102 in a direction opposite that insertion direction when engaging and moving the sheath 102 from the first position to the second position. The head end 122 may include a socket 123 for engaging an inserter or driver (not shown) when inserting the expansion member 104 into the sheath 102.

In an embodiment, the engagement feature 124 comprises outer threads 130, which may be on substantially the entirety of the length of the expansion member 104, including its insertion end 120, as seen in FIG. 1A. The outer threads 130 are designed to engage inner threads 132 disposed on the inside of the sheath's body 110. In an embodiment, the outer threads 130 may create the inner threads 132 on the inside of the sheath, e.g. if the expansion member is a central self-tapping member or screw, for example. Similar to a compression screw, the thread pitch of the outer threads 130 of the expansion member is different than the thread pitch of the inner threads 132 of the sheath 102, such that engagement of the inner and outer threads 130 and 132 moves the distal end 116 of the sheath's body 110 to the second position, thereby compressing and radially expanding the sheath 102.

Because of the buckling and longitudinal compression of the sheath 102, which radially expands the sheath 102 for fixation, it is not necessary for the expansion member 104 to increase in width along the length thereof, which is common in known expansion devices. As such, the maximum outer diameter of the expansion member 104 may be the same as or less than the minimum inner diameter of the body 110 of the sheath 102. That is, the outer diameter of the expansion device 104 does not need to be greater than inner diameter of the sheath in order to radially expand the sheath 102.

Figure 2A:
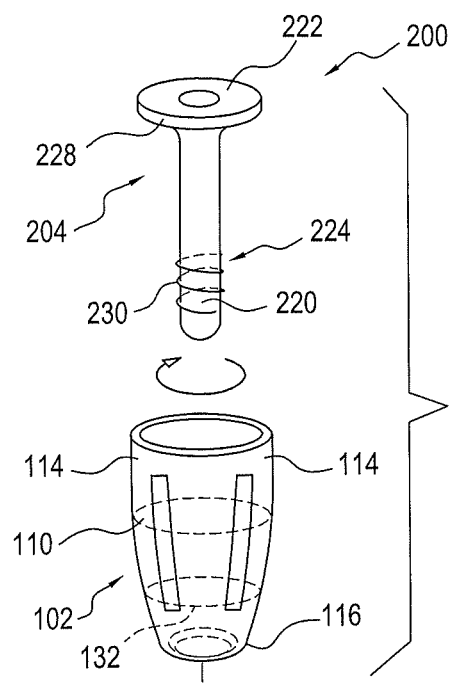
FIGS. 2A and 2B are exploded and assembled elevational views, respectively, of an example expanding implant using a central lag screw to compress and expand the outer sheath.
Figure 2B:
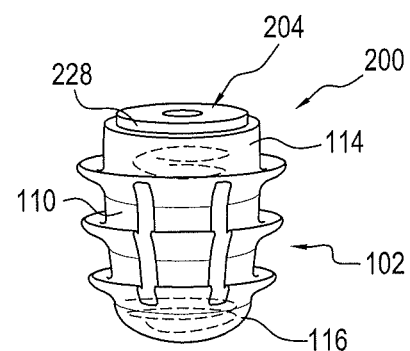

FIGS. 2A and 2B illustrate an expandable implant 200 according to another embodiment of this disclosure. The expandable implant 200 is similar to the expandable implant 100 of the above embodiment, except that the expansion member 204 of the implant 200 has an engagement feature 224 only on its insertion end 220, and its head end 222 comprises an abutment 228, such as a cap, designed to abut the proximal end 114 of the sheath 102. The engagement feature 224 is outer threads 230 that engage corresponding inner threads 132 on the inside of the body 110 of the sheath at or near its distal end 116. It should be understood, however, that the engagement feature 224 may be any type of engagement capable of coupling with the inside of the body 110 of the sheath near or at its distal end 116 in order to pull the distal end 116 of the sheath toward its proximal end 114, thereby buckling and compressing the sheath's body 110 to the second position. When pulling the distal end 116 of the sheath toward the proximal end 114 via the expansion member 204, the proximal end 114 of the sheath may abut against the cap 228 at the head end 222 of the expansion member 204.

Figure 3A:
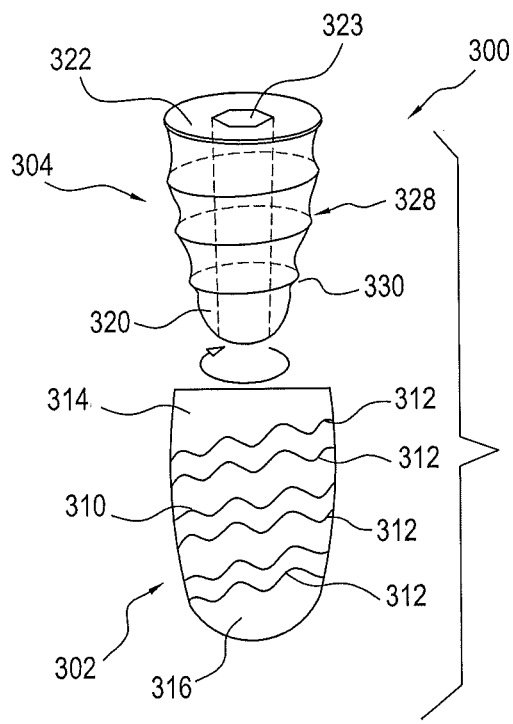
FIGS. 3A and 3B are exploded and assembled elevational views, respectively, of an example expanding implant using a central screw to radially expand a selective portion of the outer sheath.
Figure 3B:
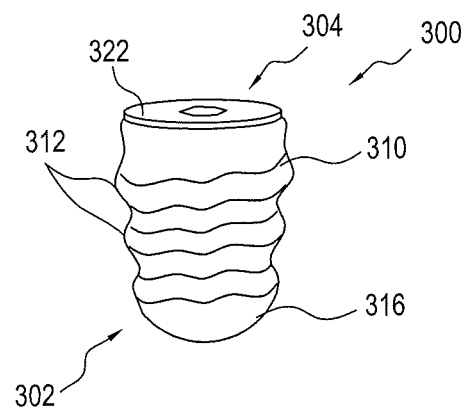

FIGS. 3A and 3B illustrate an expandable implant 300 according to another embodiment of this disclosure. Like implants 100 and 200, expandable implant 300 may comprise a sheath 302 and an expansion member 304. Sheath 302 includes a body 310 and opposite proximal and distal ends 314 and 316. Similar to sheath 102 of the above embodiments, sheath 302 may be compressed from a first position (FIG. 3A) to a second position (FIG. 3B). The body 310 of the sheath may have waveforms 312 which collapse on one another to allow the body 310 of the sheath to be compressed along the longitudinal axis of the sheath 302.

The expansion member 304 may have a tapered outer surface 328 that tapers inwardly from the head end 322 of expansion member 304 to its insertion end 320 to assist with the radial expansion of the sheath 302. The outer surface 328 may include an engagement feature, such as outer threads 330, that engage corresponding inner threads inside of the sheath's body 310 similar to the above embodiments. In this embodiment, the expansion member 304 may be inserted into the sheath 302 after the sheath has been compressed, such as by allowing the wave forms 312 of the sheath 302 to collapse. In an embodiment, the expansion member presses on the collapsed waveforms to push them radially outwardly. The head end 322 of the expansion member 304 may include a socket 323 that receives an inserter or driver when inserting the expansion member 304 into the sheath 302.

In another embodiment, an expandable implant 400 may have a sheath 402 that may collapse radially, rather than longitudinally, as seen in FIGS. 4A and 4B. That is, the sheath's body 410 may comprise of a number of forms 412 that are designed to collapse inwardly onto one another. And like the expansion member 304 of implant 300, the expansion member 404 of implant 400 may have a tapered outer surface 428 that can radially expand the sheath 402. An engagement feature, such as outer threads 430, may also be provided on the outer surface 428 of the expansion member 404 to engage corresponding inner threads 432 of the sheath's forms 412 to securely engage the expansion member 404 with the sheath 402. The sheath may also expand and be pressed against the bone tunnel walls to create the secured construct.

A tool (not shown), such as a dilator, may be used to first radially open the sheath 402 to assist with the initial insertion of the expansion member 404.

The sheaths of this disclosure may be formed of any material that is compressible or collapsible and can be radially expanded. For example, the sheaths may be formed of a polymer material and/or may be embedded with absorbable or non-absorbable polymer. In an embodiment, the body 110 of the sheath 102 may be a mesh that is overmolded with a polymer, as seen in FIG. 5, and that polymer can be absorbable or non-absorbable. In another embodiment, the 110 of the sheath 102 may be formed of one or more sutures, as seen in FIG. 6, and may have various thicknesses. For example, the body 110 may have one or more sections 140 that are thicker than other sections 142, as seen in FIG. 6, thereby allowing the other thinner sections 142 to buckle to compressing the sheath.

Figure 7:
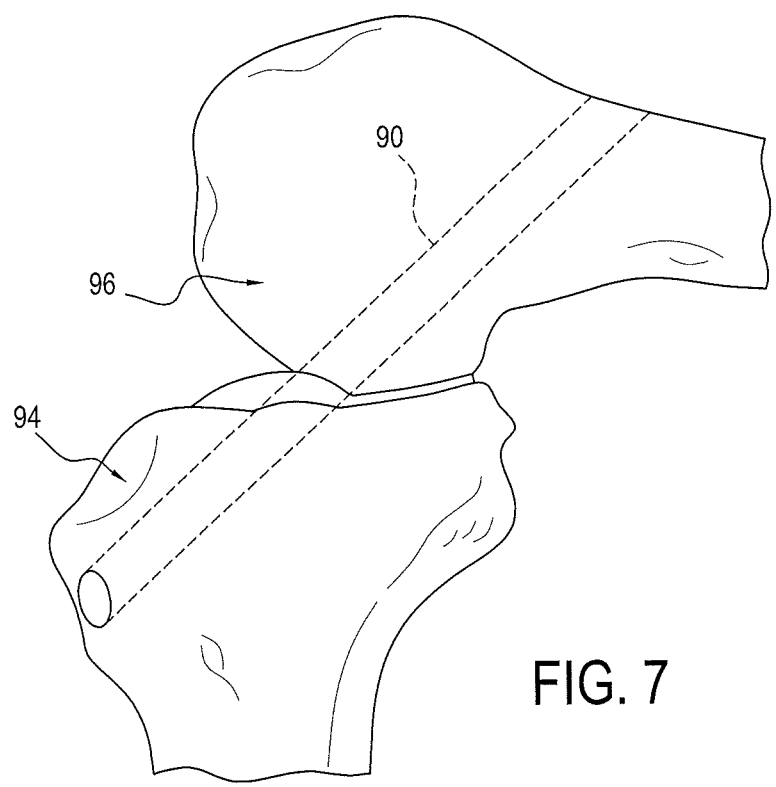
FIGS. 7-9 illustrate an example method of tissue fixation.
Figure 9:
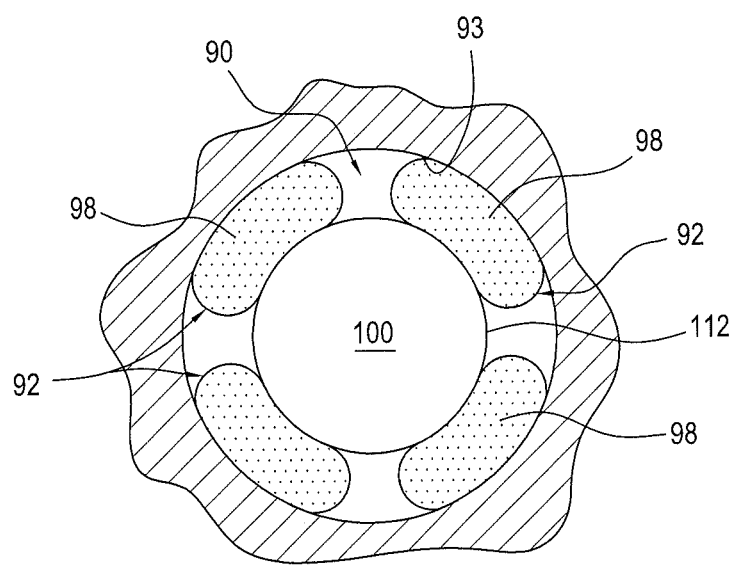
Figure 8:
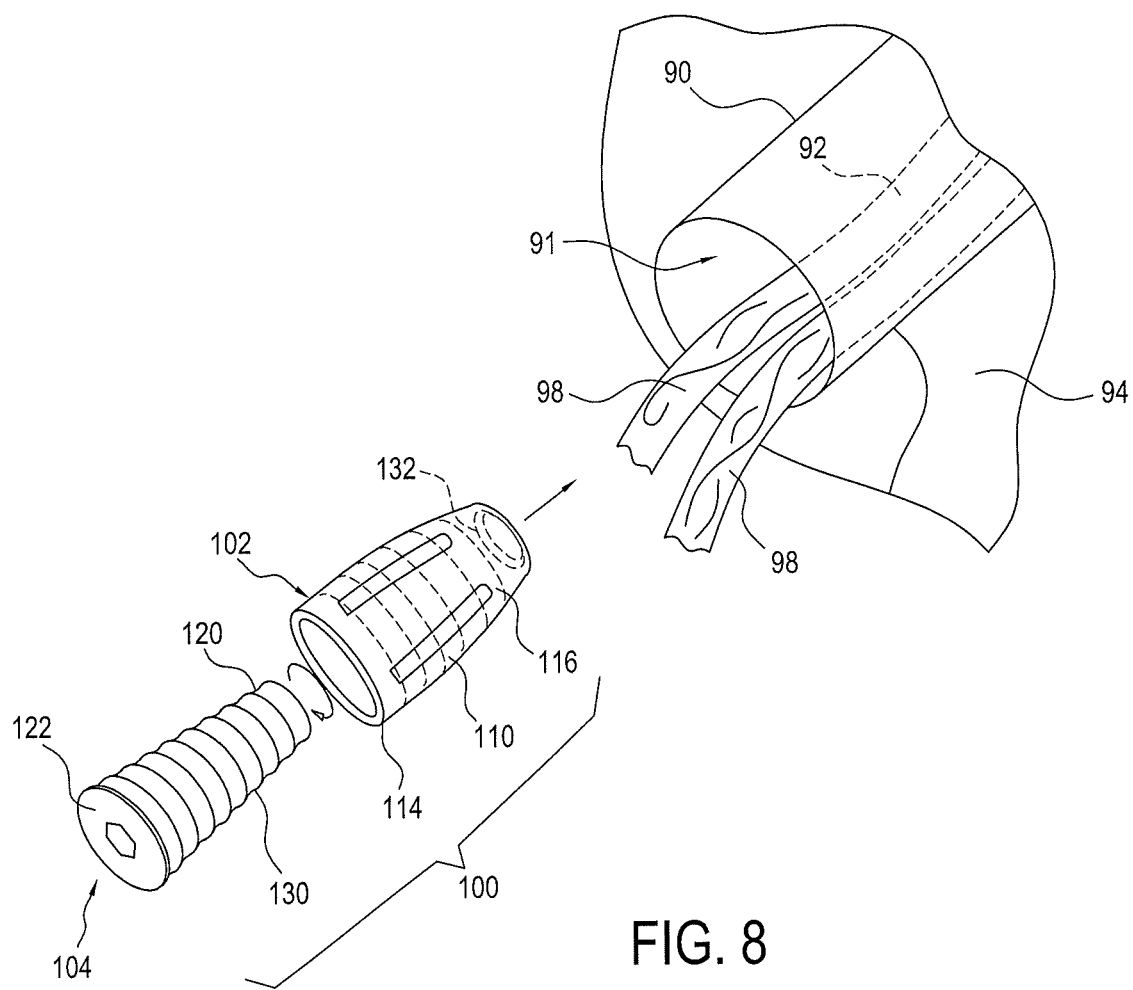

As seen in FIGS. 7-9, a method of tissue fixation according to an embodiment of this disclosure generally comprises the steps of installing a compressible sheath, such as sheath 102, into bone, as seen in FIG. 8, to capture the tissue between the sheath 102 and the bone, as seen in FIG. 9; and then inserting an expansion member, such as expansion member 104, in the body 110 of the sheath 102 in an insertion direction such that the expansion member 104 engages the distal end 116 of the sheath 102 and compresses the body 110 along the sheath's longitudinal axis 10 in a direction opposite the insertion direction, thereby radially expanding the body 110 of the sheath 102 for fixation of the tissue in the bone.

The expandable implants 100, 200, 300, and 400 and methods of this disclosure may be used for an ACL reconstruction, for example. The ACL may be reconstructed by replacing the ruptured ACL with tissue, such as a graft ligament 92, e.g. a harvested or artificial ligament or tendon. The bone tunnel 90 can be drilled through the top end of the tibia 94 and through the bottom end of the femur 96, as seen in FIG. 7. The graft 92 can then be passed through the tibial portion of bone tunnel 90, across the interior of the joint, and up into the femoral portion of bone tunnel 90 such that one end of graft ligament 92 can be secured in the femoral portion of the tunnel 90 and the other end of graft ligament 92 can be secured in the tibial portion of the tunnel 90. That will allow the two ends of the graft ligament 92 to be anchored in place so that the graft ligament 99 extends between the femur 96 and the tibia 94 in substantially the same way, and with substantially the same function, as the original ACL, to restore normal function to the knee.

The expandable implants 100, 200, 300, and 400 may be used in securing the ends of the graft ligament 92 in the bone tunnel 90. As seen in FIG. 8, the expandable implant 100, for example, can secure the end 98 of the graft 92 by installing the sheath 102, distal end 116 first, into the entrance 91 of the bone tunnel 90 such that the sheath 102 is in the first position, that is the sheath 102 has been installed in the bone tunnel and not yet compressed. Next, the expansion member 104 is inserted into the sheath 102, such as by using an inserter or driver coupled to the head end 122 of the member 104. As expansion member 104 is being inserted in the sheath, the outer threads 130 of the expansion member 104 engage the inner threads 132 near or at the distal end 116 of the sheath 102. Engagement of the outer and inner threads 130 and 132 and rotation of the expansion member 104, e.g. by using an inserter or driver, pulls the distal end 116 of the sheath 102 along its longitudinal axis toward the sheath's proximal end 114 and toward the entrance of the bone tunnel 90, thereby buckling and longitudinally compressing the sheath's body 110 to radially expand the sheath 102, thereby capturing the end 98 of the graft ligament 92 between the outer surface 112 of the implant 100 and the inner surface 93 of the bone tunnel 90, as seen in FIG. 9, to fix the same. In an embodiment, the outer threads 130 of the expansion member 104 may have a different thread pitch than that of the inner threads 132 of the sheath 102 to facilitate the pulling of the sheath's distal end 116 toward the entrance 91 of the bone tunnel 90 in the direction opposite the insertion direction of the implant. Although this disclosure may be described in the context of an ACL fixation and repair, it should be appreciated that the implants of this disclosure may also be used for any type of tissue fixation.

It should be understood that terms such as "lateral," "medial," "distal," "proximal," "superior," and "inferior" are used above consistent with the way those twits are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:
1. A tissue fixation implant, comprising:
  a compressible sheath having a body configured to capture tissue, the body having opposite proximal and distal ends, and the body being compressible along a longitudinal axis of the sheath from a first position, in which the body is not compressed, to a second position, in which the body is compressed and radially expanded; and an expansion member receivable in the body of the sheath, the expansion member having an insertion end and a head end opposite the insertion end, at least the insertion end of the body having an engagement feature configured to engage the distal end of the body of the sheath and move the distal end of the body along the longitudinal axis of the sheath from the first position to the second position.

2. The tissue fixation implant according to claim 1, wherein the body of the sheath includes one or more longitudinal slots, the one or more longitudinal slots being closed at the proximal and distal ends of the body and configured to allow radial expansion of the body.

3. The tissue fixation implant according to claim 1, wherein the body of the sheath includes a plurality of longitudinal slots radially spaced from one another, each of the longitudinal slots is closed at the proximal and distal ends of the body.

4. The tissue fixation implant according to claim 3, wherein the sheath is formed of a polymer.

5. The tissue fixation implant according to claim 1, wherein a maximum outer diameter of the expansion member is equal to or less than a minimum inner diameter of the body of the sheath.

6. The tissue fixation implant according to claim 1, wherein the engagement feature of the expansion member comprises outer threads on the insertion end.

7. The tissue fixation implant according to claim 6, wherein the outer threads of the expansion member are configured to engage inner threads on an inner diameter of the body of the sheath.

8. The tissue fixation implant according to claim 7, wherein a thread pitch of the outer threads is different than a thread pitch of the inner threads such that engagement of the inner and outer threads moves the distal end of the body of the sheath to the second position.

9. The tissue fixation implant according to claim 1, wherein the head end of the expansion member has a shoulder for abutting the proximal end of the body of the sheath.

10. The tissue fixation implant according to claim 1, wherein the body of the sheath is formed of a mesh overmolded with an absorbable or non-absorbable polymer.

11. The tissue fixation implant according to claim 1, wherein the body of the sheath is formed of one or more sutures.

12. The tissue fixation implant according to claim 11, wherein the sheath has various thicknesses.

13. The tissue fixation implant according to claim 1, wherein the compressible sheath is configured for installation in a bone tunnel in an insertion direction and the engagement feature of the expansion member moves the distal end of the body of the sheath in a direction opposite the insertion direction when moving the body of the sheath from the first position to the second position.

14. A tissue fixation implant, comprising:
a compressible sheath having a body configured to capture tissue, the body having opposite proximal and distal ends and a plurality of collapsible forms allowing the sheath to collapse from a first position, in which the body is not compressed, to a second position, in which the body is compressed; and
an expansion member receivable in the body of the sheath, the expansion member having an insertion end and a head end opposite the insertion end, the expansion member having an outer surface that tapers inwardly from the head end to the insertion end, the outer surface of the expansion member having an engagement feature configured to engage an inside of the body of the sheath,
wherein insertion of the expansion member into the body of the sheath radially expands the plurality of collapsible forms.

15. The tissue fixation implant according to claim 14, wherein the plurality of collapsible forms is wave forms that collapse longitudinally to move the sheath along a longitudinal axis thereof to the second position.

16. The tissue fixation implant according to claim 14, wherein the plurality of collapsible forms is radially collapsible forms that collapse inwardly to compress the sheath.

17. The tissue fixation implant according to claim 14, wherein the engagement feature of the outer surface of the expansion member is outer threads configured to engage inner threads on the inside of the body of the sheath.

18. A method of tissue fixation, comprising the steps of:
installing a compressible sheath of an implant into a bone tunnel to capture tissue between the sheath and the bone tunnel; and
inserting an expansion member in a body of the sheath in an insertion direction such that the expansion member engages a distal end of the sheath and compresses the body along a longitudinal axis of the sheath in a direction opposite the insertion direction, thereby radially expanding the body of the sheath for fixation of the tissue in the bone tunnel.

19. The method of claim 18, wherein inserting the expansion member into the body of the sheath includes threadably engaging an insertion end of the expansion member with the distal end of the sheath.

20. The method of claim 18, wherein outer threads of the expansion member that engage inner threads of the body of the sheath have a different thread pitch than that of the inner threads, such that the expansion member pulls the distal end in the direction opposite the insertion direction.

* * * * *